United States Patent
Oderwald et al.

(10) Patent No.: US 7,614,182 B2
(45) Date of Patent: Nov. 10, 2009

(54) METHOD FOR SEPARATING ROSETTE PLANTS

(75) Inventors: Michiel Peter Oderwald, Delft (NL); Justus Laurens Herder, Rotterdam (NL); Roland André Pieter Higler, Delft (NL)

(73) Assignee: Nederlandse Organisatie voor toegeast- Natuurwetenschappelijk Onderzoek TNO, Delft (NL)

( * ) Notice: Subject to any disclaimer, the term of this patent is extended or adjusted under 35 U.S.C. 154(b) by 501 days.

(21) Appl. No.: 10/528,026

(22) PCT Filed: Sep. 15, 2003

(86) PCT No.: PCT/NL03/00610

§ 371 (c)(1),
(2), (4) Date: Sep. 27, 2005

(87) PCT Pub. No.: WO2004/023863

PCT Pub. Date: Mar. 25, 2004

(65) Prior Publication Data

US 2006/0112619 A1    Jun. 1, 2006

(30) Foreign Application Priority Data

Sep. 16, 2002  (NL) .................................. 1021463

(51) Int. Cl.
*A01B 79/00* (2006.01)
*A01B 79/02* (2006.01)
*A01C 1/00* (2006.01)
*A01G 1/00* (2006.01)
*A01H 3/00* (2006.01)

(52) U.S. Cl. .............................. 47/58.1 R; 47/58.1 CF; 47/6

(58) Field of Classification Search .................. 47/1.43, 47/55, 58.1 CF, DIG. 3, 10, 6; *A01G 03/02, A01G 03/08, 03/00*
See application file for complete search history.

(56) References Cited

U.S. PATENT DOCUMENTS 2,167,337 A * 7/1939 De Meester .............. 47/1.01 R
2,681,504 A * 6/1954 Fox .............................. 30/123

(Continued)

FOREIGN PATENT DOCUMENTS

EP           532064 A2 *  3/1993
WO    WO 88/04520        6/1988
WO    WO 91/18499       12/1991

*Primary Examiner*—Rob Swiatek
*Assistant Examiner*—Kristen C Hayes
(74) *Attorney, Agent, or Firm*—Young & Thompson

(57) ABSTRACT

A method for separating a lump piece of rosette plants. The method includes the steps of gripping a rosette plant and positioning it parallel to a longitudinal axis of an elongated holder which has a longitudinal opening at least along the longitudinal axis; introducing a part of the lump piece of the rosette plant into the holder via the mentioned longitudinal opening; cutting off the lump piece along a cutting plane parallel to the longitudinal axis, while closing the longitudinal opening, such that the introduced part of the lump piece is enclosed in the holder; and removing the enclosed cut-off part of the lump piece from the holder. The method includes the further step of cutting off a part of the rosette plant enclosed in the holder along a second cutting plane.

17 Claims, 4 Drawing Sheets

U.S. PATENT DOCUMENTS

| | | | | |
|---|---|---|---|---|
| 4,098,020 A | * | 7/1978 | Cook | 47/6 |
| 4,361,959 A | * | 12/1982 | Akerson | 30/231 |
| 5,370,713 A | | 12/1994 | Hanseler | |
| 5,899,019 A | * | 5/1999 | Groves | 47/1.01 R |
| 2004/0118041 A1 | * | 6/2004 | Rombouts et al. | 47/58.1 CF |
| 2005/0246948 A1 | * | 11/2005 | Sowinski | 47/6 |

* cited by examiner

METHOD FOR SEPARATING ROSETTE PLANTS

This is a 371 National Stage application of International application no. PCT/NL2003/000610, filed Sep. 15, 2003, which claims priority to application no. NL 1021463, filed Sep. 16, 2002. The entire contents of the above-referenced applications are hereby incorporated by reference in their entirety.

The invention relates to a method and apparatus for separating a lump piece of rosette plants. Such a method and apparatus are used during the asexual multiplication (propagation by cuttings) of rosette plants.

BACKGROUND OF THE INVENTION

A rosette plant is roughly built up from a basis of growing points from which new leaves and roots grow. In an adult plant, this basis is relatively large in size and comprises a large number of sprouted leaves. By placing a part of the rosette plant in a specific medium, growing points or other plant parts can be incited to form shoots. In this manner, a lump piece of rosette plants is formed, designated below as "lump piece". The asexual multiplication takes place by cutting this lump piece into parts and placing the individual parts on a growing medium. These parts form new shoots, which again form a new lump piece, so that a multiplication process results, which can be repeated several times. In this manner, many, up to as many as thousands of, copies can be cultured from one single plant. This process is referred to as plant multiplication.

Although this process is substantially relatively simple in nature, the practical conditions in which the process is carried out are of great importance to be able to realize a sufficiently large and germ-free yield. It is crucial, then, to check the ambient conditions; in particular, it is important that the multiplication nearly always takes place sterilely. In addition, the separation of the lump piece is relatively difficult, because the lump often has a diverging shape and size, and because it is of importance to damage growing points as less as possible. A damaged cutting will show a decreased growth on the damaged parts, so that the occurrence of damage during separation has a relatively large negative effect on the yield. These problems have resulted in that contrary to automated multiplication techniques for other types of plants, such as stem plants, for rosette plants satisfactory techniques enabling the multiplication to be carried out automatically have not been developed as yet.

SUMMARY OF THE INVENTION

The invention has for its object to remove these problems and to provide a method and apparatus with which automated processing is possible. This object is achieved by a method of the type referred to in the opening paragraph, which further comprises the steps of gripping a rosette plant and positioning it parallel to a longitudinal axis of an elongated holder, which comprises a longitudinal opening at least along the longitudinal axis; introducing a part of the lump piece of the rosette plant into the holder via the mentioned longitudinal opening; cutting off the lump piece along a cutting plane parallel to the longitudinal axis while closing the longitudinal opening, such that the introduced part of the lump piece is enclosed in the holder; and removing the enclosed cut-off part of the lump piece from the holder.

It is observed that the introduction of plant material into a holder is known from the International application WO 91/18499. This application, however, relates to the multiplication of stem plants in which a single node is pressed through a circular cut in the holder. This method, however, is in no way transferable to the culture of rosette plants, because here the individual nodes cannot be identified, but are grown together into one lump-shaped part.

Because the method makes use of the enclosure of the plant in a holder under simultaneous separation thereof, in the holder a cutting is enclosed which is relatively uniform in size and can relatively easily be processed further from this holder.

In a preferred embodiment, the method comprises the further step of cutting a cut-off part of the rosette plant enclosed in the holder along a second cutting plane. In particular, this is important in the multiplication phase in which the sprouting stems are cut off.

In a further preferred embodiment, the removal from the holder can take place while retaining orientation. Thus, it can be effected, for instance, that the cut-off cutting is introduced into a growing medium in the right orientation, that is to say with the sprout points in a direction remote from the growing medium.

In another preferred embodiment, the cutting off of the lump piece is carried out by the rotation of two half-round sections engaging each other along a longitudinal axis, during which the sections cuttingly glide along each other, such that after rotation the sections form a cylinder in which the part of the lump piece is received. It is observed that such cutting sections are known per se, for instance from U.S. Pat. No. 5,843,106. This application, however relates to an apparatus for taking biopts from human tissue.

In a further embodiment, the method comprises the blowing out of the cut-off part of the lump piece enclosed in the holder, by means of compressed air.

The application further relates to an apparatus for separating the lump piece of rosette plants, comprising: an elongated holder which comprises a longitudinal opening at least along the longitudinal axis; and a first cutting element for cutting off a lump piece along a cutting plane parallel to the longitudinal axis while closing the longitudinal opening, such that an introduced part of the lump piece is enclosed in the holder.

The apparatus may comprise a computer-controlled gripper for positioning the rosette plant. In a semi-automated embodiment, it is also possible, however, that the rosette plants are manually introduced into the apparatus, or that a person manually introduces the cutting places or the location of the shoots on the plant into the system. A further embodiment relates to an apparatus which comprises a transverse opening oriented transversely to the longitudinal axis. This transverse opening can be used to axially introduce the lump piece into the apparatus. Alternatively, the lump piece may be introduced radially, via the mentioned longitudinal opening. A combination of both directions is of course also possible. In addition, the apparatus may comprise a second cutting element for cutting off a cut-off part of the rosette plant enclosed in the holder along a second cutting plane transverse to the longitudinal axis while closing the transverse opening.

The holder may have such a cross-section that in enclosed condition the cut-off part is clampingly enclosed, so that upon removal a cut-off part retains its orientation.

In a preferred embodiment, the elongated holder comprises a first half-round section, and the cutting element comprises a second half-round section, which first and second sections engage each other along a rotation axis and carry out a cutting movement upon rotation, such that after rotation the sections form a cylinder in which a part of a cut-off lump piece can be received.

The apparatus may comprise an expelling element for removing the enclosed cut-off part of the lump piece from the holder. Furthermore, the expelling element may be arranged to expel the cut-off part along the longitudinal axis of the holder. Advantageously, the expelling element comprises an outflow longitudinal opening oriented along the longitudinal axis of the holder for blowing out compressed air. The outflow longitudinal opening may be provided in the second cutting element, so that the cutting element, after having carried out a cutting movement, positions the outflow longitudinal opening such that the cut-off part can be blown out. The second cutting element may be connected with a pair of parallel-arranged leaf springs.

The invention further relates to an automated culturing apparatus, in which an apparatus according to one of the above-mentioned aspects is included, and further comprising image recognition means for identifying a rosette plant to be multiplied;

a gripper for gripping the rosette plant and positioning it;

an apparatus according to one of the above-mentioned aspects, which cuts off and encloses the plant under control of the image recognition means;

transport and manipulation means for transporting and manipulating the growing medium, into which the cut-off cutting is introduced;

control means for controlling the gripper, the apparatus according to one of the above-mentioned aspects, and the transport and manipulation means under control of the image recognition means.

BRIEF DESCRIPTION OF THE DRAWINGS

The invention will be explained in more detail with reference to the drawing.

In this drawing.

In the Figures similar or corresponding parts are indicated by the same reference numerals.

DETAILED DESCRIPTION OF THE INVENTION

Figure 1:
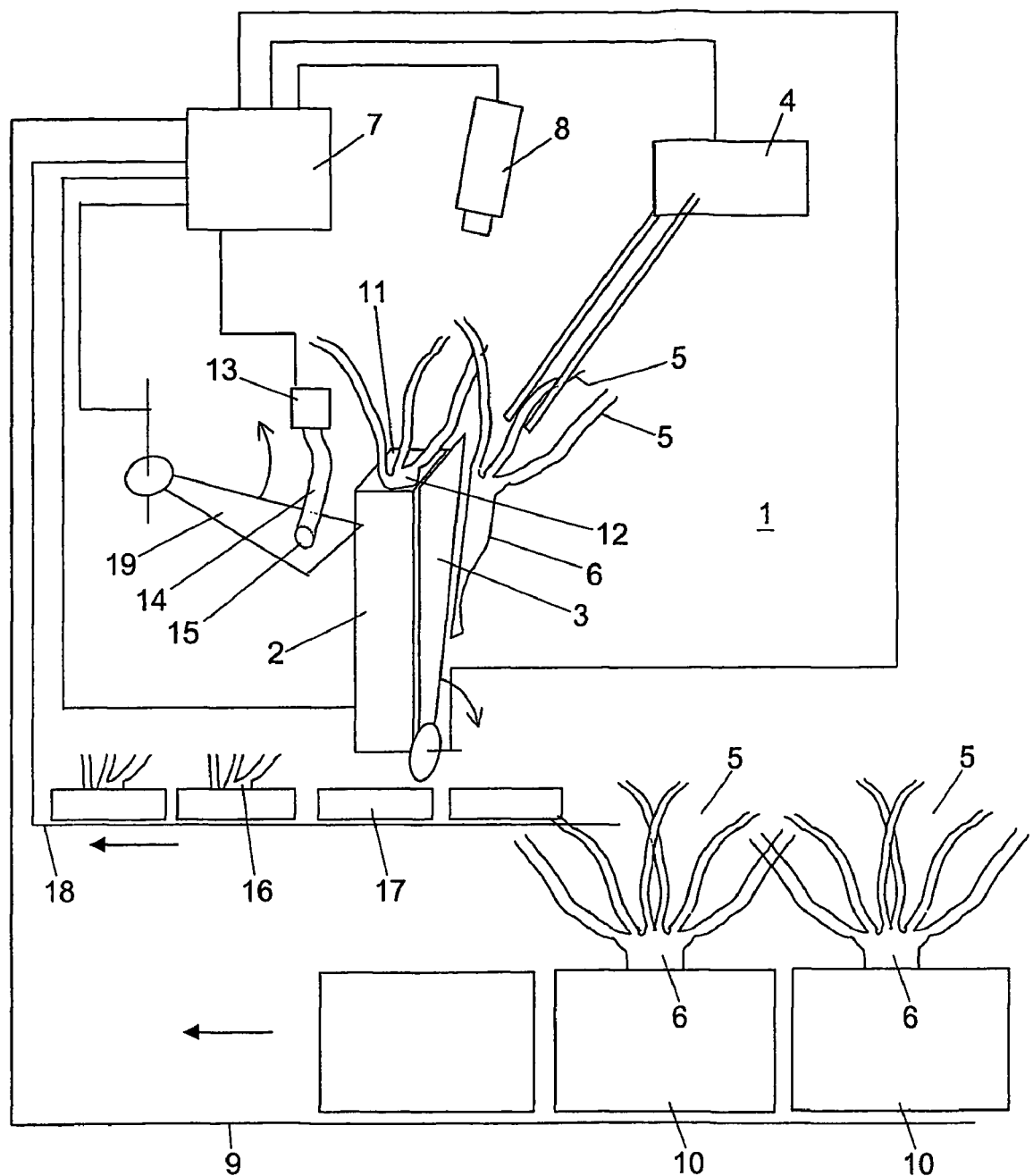
FIG. 1 shows a system structure of an automated culturing system according to the invention.

FIG. 1 shows an automated culturing system 1 for culturing rosette plants according to the invention. The apparatus is built up from an elongated holder 2 and a cutting element 3. The holder 2 has a longitudinal opening (which is not visible in the Figure, because it is closed by the cutting element 3), as will be explained in more detail with reference to FIGS. 3, 5, and 6. The cutting element 3 is arranged to cut off a lump piece while enclosed in the holder 2, as shown in FIG. 1. Meanwhile, the lump piece is held by a gripper 4, which grips, for instance, the stems 5 of a lump piece 6. The gripper 4 is controlled by a central processor 7, which is coupled with an image recording system 8 for identifying a lump piece 6 to be cut off and for carrying out a relative movement of the lump piece 6 and the holder 2, so that the lump piece 6 can be introduced into the holder 2.

Before introducing the lump piece 6 into the holder 2, it is taken up by the gripper 4 from a conveyor belt 9, on which trays 10 are placed with a growing medium (not shown), in which lump pieces 6 to be separated are grown.

The lump piece 6 is positioned parallel to the holder, that is to say, an axis running from the growing points to the leaves runs substantially parallel to the longitudinal axis of the holder 2. The lump piece 6 is then introduced into the holder 2 in a radial movement. If in the case as shown in FIG. 1 the holder has a transverse opening 11, the lump piece can also be introduced via an axial movement, or by a combination of both movements. Alternatively, the lump piece may be fixed, and the holder may be manipulated so as to introduce the lump piece into the holder.

All this takes place under control of the processor 7 while fed by signals from the image recording device 8. If the lump piece is positioned in the holder in the right manner, it is cut off by the cutting element 3 parallel to the longitudinal axis of the holder 2 while closing it, so that the introduced part 12 of the lump piece 6 is enclosed in the holder 2. It is observed that in this connection the term "enclosing" means that the holder, optionally in combination with the cutting element, forms an enclosure for the cut-off lump piece. It is not important, then, if the lump piece 6 is held in the holder 2 completely around, optionally in combination with the cutting element 3, that is to say along a longitudinal circumference of a plane transverse to the longitudinal axis of the holder 2. It is sufficient that the holder 2, in combination with the cutting element 3, can hold the lump piece, preferably in an orientation retaining manner.

The apparatus 1 shown in FIG. 1 further comprises an expelling device in the form of a compressed air device 13, which is connected by a hose 14 with a nozzle 15. After cutting off the lump piece 6, the nozzle 15 is located above the holder 2, so that by blowing compressed air through the nozzle 15, the cut-off lump piece 16 can be blown out parallel to the longitudinal axis of the holder 2 at the bottom side. By properly dimensioning the holder 2, the lump piece 6 can be blown out while retaining orientation. As a result, it lands in a collecting tray 17 moved below the holder 2, in which it can be introduced into a growing medium (not shown) in the right orientation. The collecting tray 17 is moved on by a conveyor belt 18, preferably under control of the processor 7.

In the preferred embodiment shown in FIG. 1, the nozzle is formed on a second knife 19, which can cut off the stems from the lump piece 6, after it has been enclosed in the holder. The second knife 19 moves in a cutting plane oriented transversely to the longitudinal axis of the holder 2 and is also controlled by the processor 7.

Figure 2:
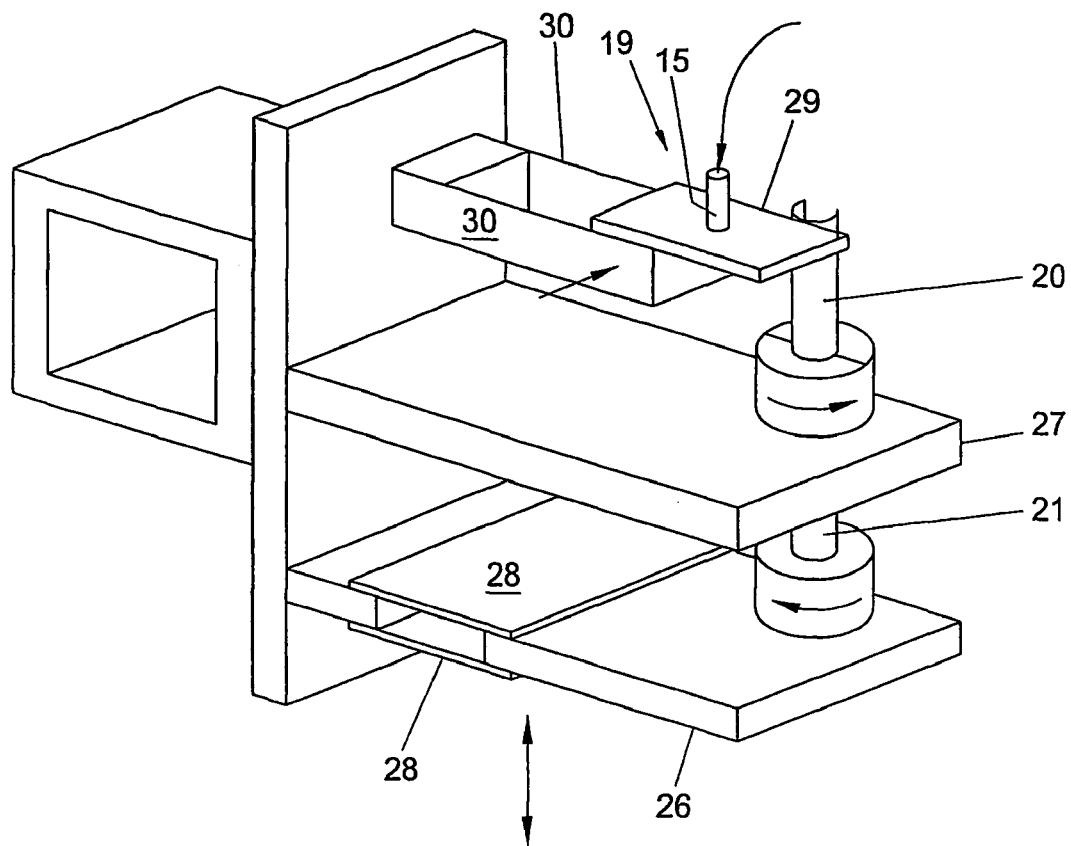
FIG. 2 shows a first embodiment of the apparatus according to the invention.
Figure 3:
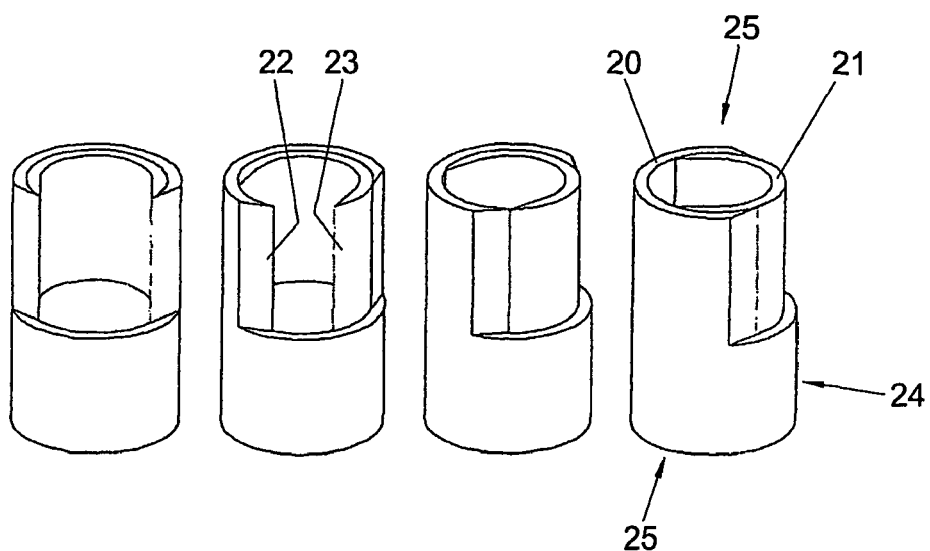
FIG. 3 shows a schematic detailed representation of the rotating knives in FIG. 2.

Referring to FIGS. 2 and 3, a preferred embodiment of the holder 2 shown in FIG. 1 will now be discussed in more detail. This holder 2 is formed by two half-round sections 20 and 21 engaging each other. The sections 20, 21 may be identical in form, that is to say different only in size, with an inner section having a smaller cross-section than an outer section. In this connection, it is observed that in this embodiment the holder 2 and the cutting element 3 may actually have the same appearance. In addition, it is so that a section 20 may be fixedly provided with a sharp edge 22 along a longitudinal side, optionally in combination with the second section 21, which may also be provided with a sharp edge 23. Furthermore, it may be that only one of both sections 20 or 21 has a sharp cutting edge, while it is even possible that the holder and the cutting edge are fixedly formed on one of the parts, and that the "cutting element" itself only performs a pushing function for pushing the root lump against a sharp edge of the holder. Such variants are also considered to fall within the scope of protection of the claims. According to FIGS. 2 and 3, the sections 20, 21 are designed such that they carry out a rotation relative to each other, while cuttingly gliding along each other, after which rotation a cylinder 24 is formed, in which the part of the lump piece 6 is received. Preferably, the sections are open on the transverse sides 25, so that the formed cylinder 24 is open. As a result, the cut-off lump piece can be axially removed from the cylinder. Optionally, the lump piece to be cut off may be axially introduced into the half-round sections 20, 21.

As shown in FIG. 2, the inner section 21 and the outer section 20 may be mounted on different holder plates 26 and 27. One plate 26 may be resiliently designed, for instance with parallel leaf springs 28. Thus, an axial movement of section 20 relative to section 21 can be effected during the rotation of the sections 20, 21. As a result, a purer cut can be obtained, which, in view of the nature of the material, is of great importance to the yield.

Figure 4:
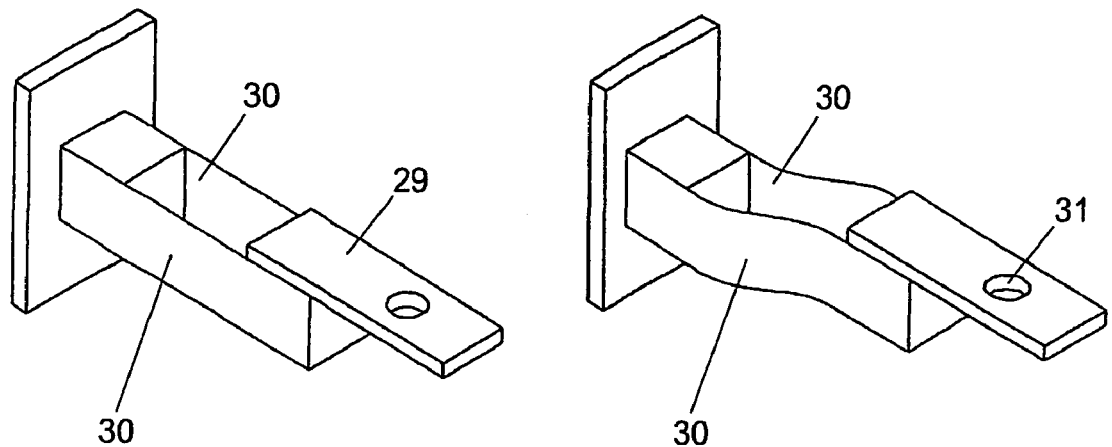
FIG. 4 shows a schematic detailed representation of a second knife placed transversely to the rotating knives.

Referring to FIG. 4, a preferred embodiment of the second knife 19 will now be discussed, which moves in a cutting plane transverse to the longitudinal axis of the holder 2 and/or sections 20, 21. The knife 19 comprises a flat cutting plate 29, which is also mounted on a set of leaf springs 30, which are oriented parallel. By carrying out a pushing movement transversely to the leaf springs, by means of, for instance, a translating arm (not shown), the cutting plate 29 can be moved in transverse direction and be brought above the holder 2, in a manner as can be derived from FIG. 2. Provided in the cutting plate 29 is an opening 31, to which a nozzle 15 is connected, see FIG. 2. At a position arranged above the holder 2, compressed air can be blown out of the compressed air device 13 through the nozzle 15, under control of the processor 7. The cut-off lump piece 16 can thus be axially removed from the holder 2, preferably while retaining orientation.

Figure 5:
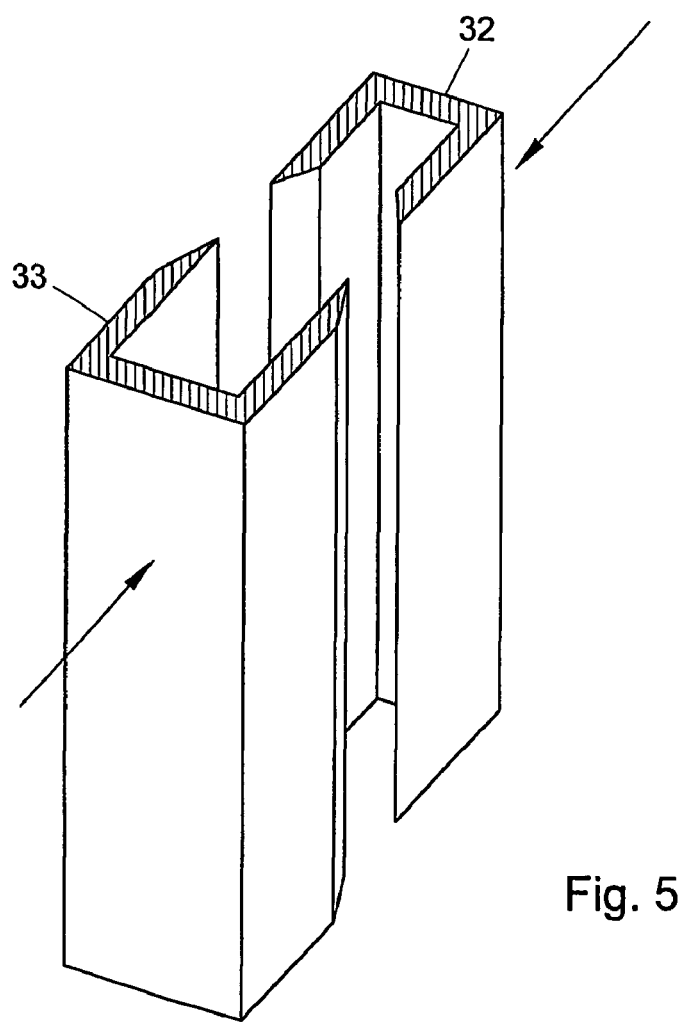
FIG. 5 shows an alternative embodiment of the apparatus according to the invention.
Figure 6:
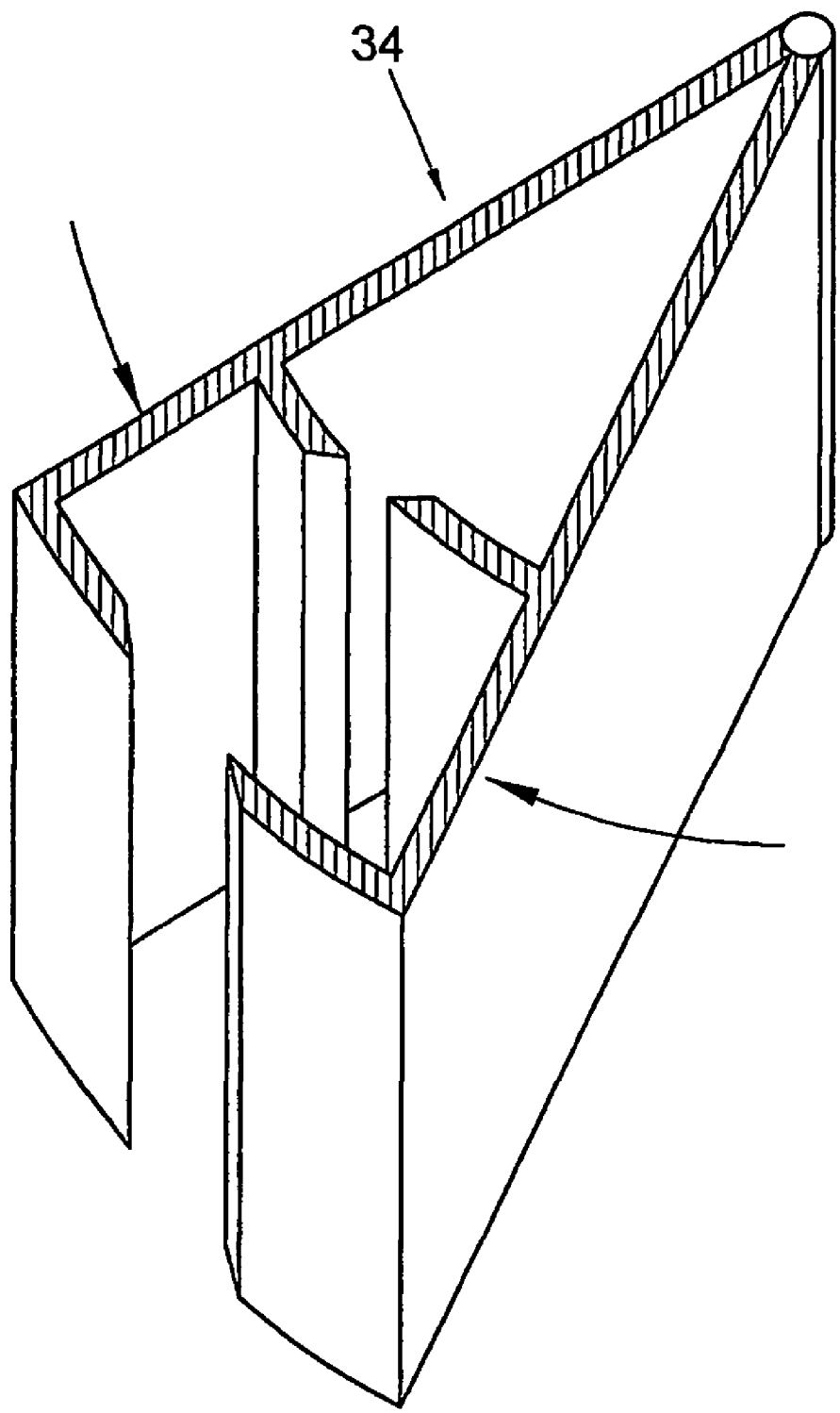
FIG. 6 shows a second alternative embodiment of the apparatus according to the invention.

Finally, FIGS. 5 and 6 show alternative embodiments of the holder and the cutting element. These embodiments relate to a substantially symmetrically designed combination of a holder/cutting element in the form of two correspondingly formed U-shaped sections 32 and 33 with a sharp longitudinal side. By laying the root lump along one of the sections 32 or 33 and blanking the other on, over, or in it, a part of the lump is cut off and enclosed in the elongated sections 32 and 33. In a manner similar to that discussed with reference to FIGS. 1-4, the enclosed part can be removed from the sections and be placed in a growing medium. Finally, FIG. 6 shows a tong structure 34, which can be mechanically or optionally manually operated, to move the sections 32 and 33 toward each other. Such a tong structure is—slightly modified—of course also possible to operate the rotating sections shown in FIGS. 2 and 3.

The invention is not limited to the exemplary embodiments shown in the Figures, but may comprise all kinds of variations and modifications thereof. For instance, in the exemplary embodiments the lump piece is moved to the holder. Of course, arrangements are also possible in which the holder is moved to the lump piece. Furthermore, the invention is not only limited to rosette plants in the strictly biological sense, but also comprises a method and apparatus for plants which, in a specific culturing stage, possess a similar rosette plant structure, that is to say, a basis of growing points from which new leaves and roots grow, which basis can be multiplied by splitting. Such variations are considered to be within the scope of the invention as defined by the following claims.

The invention claimed is:

1. A method for separating a lump piece of a rosette plant, said method comprising:
   gripping said rosette plant and positioning said rosette plant parallel to a longitudinal axis of an elongated holder, which comprises a longitudinal opening at least along the longitudinal axis;
   introducing a lump piece of said rosette plant into the holder by way of said longitudinal opening;
   with a cutting element, cutting off the lump piece along a cutting plane parallel to the longitudinal axis, while closing the longitudinal opening, so that the introduced cut-off lump piece is enclosed in the holder, such that the holder encloses the introduced part of the lump piece, at least in combination with the cutting element, along a substantially complete circumference around the longitudinal axis of the holder, so that a sprout remains pointing in a direction remote from a growing medium; and
   removing the enclosed cut-off lump piece from the holder.

2. The method according to claim 1, further comprising cutting off a cut-off part of the lump piece of the rosette plant enclosed in the holder along a second cutting plane.

3. The method according to claim 1, wherein the removal of the cut-off piece from the holder takes place while said cut-off piece remains pointing in a direction remote from the growing medium.

4. The method according to claim 1, wherein the cutting off of the lump piece is performed by rotation of two half-round sections engaging each other along a rotation axis, during which the sections cuttingly glide along each other, such that after rotation the sections form a cylinder in which the cut-off lump piece is received.

5. The method according to claim 1, further comprising a step of blowing out the cut-off lump piece enclosed in the holder using compressed air.

6. An apparatus for separating a lump piece of a rosette plant, said apparatus comprising:
   an elongated holder which comprises a longitudinal opening at least along the longitudinal axis; and
   a first cutting element for cutting off a lump piece of said rosette plant along a cutting plane parallel to the longitudinal axis, while closing the longitudinal opening, so that an introduced part of the cut-off lump piece is enclosed in the holder, such that the holder enclosed the introduced part of the lump piece, at least in combination with the cutting element, along a substantially complete circumference around the longitudinal axis of the holder, so that a sprout remains pointing in a direction remote from a growing medium.

7. The apparatus according to claim 6, wherein the apparatus comprises a transverse opening which is oriented transversely to the longitudinal axis.

8. The apparatus according to claim 7, wherein the apparatus comprises a second cutting element for cutting off a part of the rosette plant enclosed in the holder along a second cutting plane transversely to the longitudinal axis, while closing the transverse opening.

9. The apparatus according to claim 8, wherein the second cutting element is connected to a backplane of the apparatus with a pair of parallel-arranged leaf springs.

10. The apparatus according to claim 6, wherein the holder has a cross-section and is arranged so that, when in an enclosed condition, the cut-off lump piece is clampingly enclosed, so that upon removal the cut-off lump piece remains pointing in a direction remote from the growing medium.

11. The apparatus according to claim 6, wherein the elongated holder comprises a first half-round section, and the first cutting element comprises a second half-round section, which first and second sections engage each other along a rotation axis and, upon rotation, carry out a cutting movement, so that after rotation the sections form a cylinder in which a part of the cut-off lump piece can be received.

12. The apparatus according to claim 11, wherein the sections are arranged to carry out an axial movement relative to each other during the rotation.

13. The apparatus according to claim 6, wherein the apparatus comprises an expelling element for removing the enclosed cut-off lump piece from the holder.

14. The apparatus according to claim 13, wherein the expelling element is arranged to expel the cut-off lump piece along the longitudinal axis of the holder.

15. The apparatus according to claim 14, wherein the expelling element comprises an outflow longitudinal opening oriented along the longitudinal axis of the holder for blowing out compressed air.

16. The apparatus according to claim 15, wherein the outflow longitudinal opening is provided in a second cutting element, so that the second cutting element, after having carried out a cutting movement and having cut-off stems from the lump piece, positions the outflow longitudinal opening so that the cut-off lump piece can be blown out by using compressed air.

17. An automated apparatus, comprising:
  image recognition means for identifying a rosette plant to be multiplied;
  a gripper for gripping the rosette plant and positioning the rosette plant;
  an apparatus according to claim 6, which cuts off and encloses the rosette plant;
  transport and manipulation means for transporting and manipulating a growing medium, into which the cut-off plant is introduced; and
  control means for controlling the gripper, the apparatus, and the transport and manipulation means under control of the image recognition means.

* * * * *

UNITED STATES PATENT AND TRADEMARK OFFICE
CERTIFICATE OF CORRECTION

PATENT NO.        : 7,614,182 B2                                Page 1 of 1
APPLICATION NO.   : 10/528026
DATED             : November 10, 2009
INVENTOR(S)       : Michiel Peter Oderwald et al.

It is certified that error appears in the above-identified patent and that said Letters Patent is hereby corrected as shown below:

On the title page, please amend item (73) to read as follows:

--(73) Assignee: Nederlandse Organisatie voor toegepast-Natuurwetenschappelijk Onderzoek TNO, Delft (NL)--

Signed and Sealed this

Ninth Day of February, 2010

David J. Kappos
*Director of the United States Patent and Trademark Office*

UNITED STATES PATENT AND TRADEMARK OFFICE
CERTIFICATE OF CORRECTION

PATENT NO. : 7,614,182 B2 Page 1 of 1
APPLICATION NO. : 10/528026
DATED : November 10, 2009
INVENTOR(S) : Oderwald et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 822 days.

Signed and Sealed this

Nineteenth Day of October, 2010

David J. Kappos
*Director of the United States Patent and Trademark Office*